United States Patent
Hoffmann et al.

(10) Patent No.: US 6,284,939 B1
(45) Date of Patent: Sep. 4, 2001

(54) PROCESS FOR LIQUID-PHASE CONVERSION WITH A MOVING-BED CATALYST USING A STRIPPER-LIFT

(75) Inventors: Frédéric Hoffmann, Paris; Philippe Mege, Reventin Vaugris; Dominique Commereuc, Meudon, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/363,817

(22) Filed: Jul. 30, 1999

(30) Foreign Application Priority Data

Jul. 31, 1998 (FR) .................................................. 98/09823

(51) Int. Cl.⁷ ...................................................... C07C 6/02
(52) U.S. Cl. .................... 585/643; 585/645; 585/646; 585/647; 585/921
(58) Field of Search ..................... 585/643, 645–647, 585/921; 422/144, 145, 213, 214

(56) References Cited

U.S. PATENT DOCUMENTS

| 2,465,255 | * | 3/1949 | Moorman | 196/52 |
| 2,709,673 | * | 5/1955 | Berg | 196/52 |
| 3,365,513 | * | 1/1968 | Heckelsberg | 260/683 |
| 3,978,150 | * | 8/1976 | McWilliams, Jr. | 260/683.3 |
| 4,615,792 | * | 10/1986 | Greenwood | 208/134 |
| 4,981,575 | * | 1/1991 | Bonneville | 208/64 |

FOREIGN PATENT DOCUMENTS 2 608 595 * 6/1988 (FR) .

* cited by examiner

Primary Examiner—Marian C. Knode
Assistant Examiner—Thuan D. Dang
(74) Attorney, Agent, or Firm—Millen, White, Zelano & Branigan, P.C.

(57) ABSTRACT

This invention pertains to a continuous catalytic process, for example, for the metathesis of olefins that uses a catalyst circulating in a moving bed in at least one reaction zone operating in the liquid phase and in a regenerator, with a lift to transfer the deactivated catalyst emerging from the reaction zone to the regenerator, whereby said process is characterized by the fact that the transfer is accomplished by a gas that does not react with the catalyst and with the stripping off of at least a portion of the organic matter that is adsorbed on the deactivated catalyst.

25 Claims, 1 Drawing Sheet

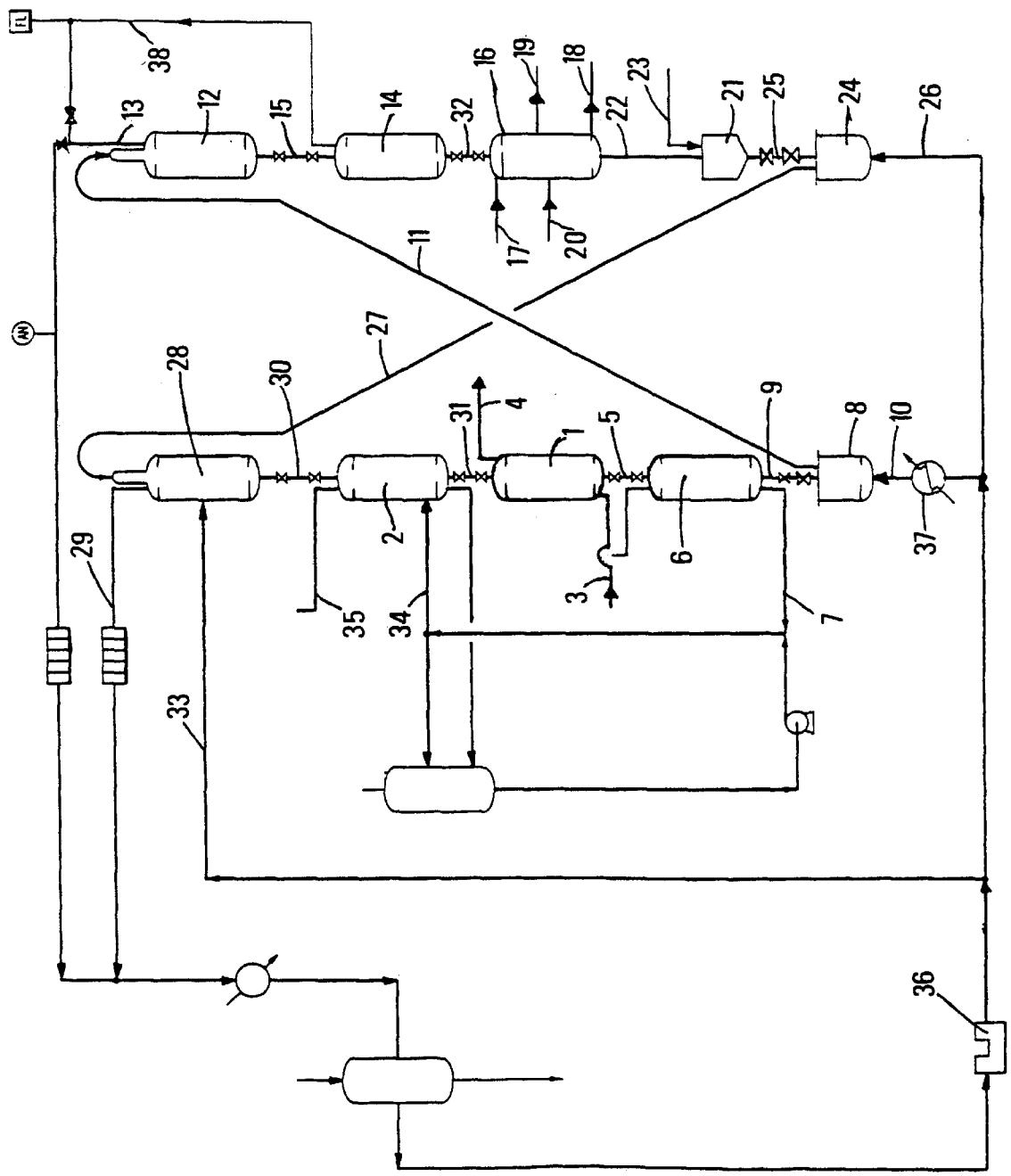

PROCESS FOR LIQUID-PHASE CONVERSION WITH A MOVING-BED CATALYST USING A STRIPPER-LIFT

The invention pertains to a catalytic process that uses a down-flowing catalyst in the form of a moving bed in at least one reaction zone and a regenerator. The catalyst that comes from the reaction zone and, in general, from the last reaction zone is at least partially deactivated by the presence of organic matter.

Said organic matter includes coke, gums, and the adsorbed organic matter, which are adsorbed hydrocarbons in the case of a process that treats petroleum fractions.

The coke and gums are formed from the adsorbed organic matter and turn into deposits on the catalyst. Gums and coke shall be excluded from the meaning of the term "adsorbed organic matter."

In order to reactivate the catalyst, it is necessary to transfer it into the regenerator, which comprises at least one regeneration zone in which, in a first stage, the organic matter is eliminated from the catalyst, whereby the catalyst may undergo other types of treatment.

The elimination of the organic matter is generally done with combustion, in one or more zones.

It has been found that, in certain processes such as metathesis that operate in the liquid phase, the catalyst is very sensitive to the adsorbed organic matter, which is hydrocarbons in the case of metathesis.

When the organic-matter contents are high, they can even exceed 50% of the weight of the catalyst, for example 70%.

Such quantities cannot, however, be burned in installations that generally can handle up to 8–10% organic matter to be burned, which is essentially coke.

The applicant has found that the adsorbed organic matter, for example, in the metathesis process essentially includes relatively light hydrocarbons. As a matter of fact, the preferred olefins that are likely to react under conditions of metathesis are olefins that have 2–40 carbon atoms and generally 2 to 10 carbon atoms. The existing processes operate essentially on fractions C4, C5, C6 or even fractions that contain C18–C30 olefins.

Patent FR 2.608.595 describes a process for metathesis of olefins in a moving bed, in which the catalyst is transferred by a lift from the reaction zone to the regenerator, whereby the regenerated catalyst is brought back up to the reaction zone by a lift with a liquified gas. It was thus necessary to add an additional stage for the elimination of a large portion of the adsorbed matter prior to regeneration or to provide for more combustion zones in the regenerator.

One solution would involve desorbing a portion of the organic matter by heat exchange between the solid and a high-temperature gas, followed by drainage-depressurization phases.

The applicant has found, however, that this technique was attended by major drawbacks: poor heat exchange between the gas and catalyst particles, elevated gas temperature, the need for high gas flow rates and a technology that is difficult to implement owing, in particular, to the presence of an exchanger which has difficulty tolerating the necessary gas pressurization-depressurization cycles.

Moreover, in these liquid-phase processes such as metathesis wherein the catalyst is quickly deactivated, regeneration has to be done continuously, and the presence of such an exchanger would further impede this circulation.

The reaction-regeneration operations are well-known, for example in connection with reforming that operates in the gas phase (EP-439,388 or U.S. Pat. No. 3,839,197). The catalyst that emerges from the last reaction zone is picked up in a lift pot that also receives a gas (hydrogen, nitrogen, . . . ) which brings the catalyst in the lift to the receptacle located at the top of the regenerator. The catalyst that emerges from the regenerator is carried by lift gas up to the top of the first reaction zone.

Surprisingly enough, the applicant found that it was possible to eliminate a significant portion of the adsorbed organic matter without an additional stage and without additional combustion zones by stripping the adsorbed organic matter in the lift itself that brings the catalyst from the reaction zone to the regenerator.

What was particularly surprising was that it was found that the stripper-lift could be effective even at fairly low temperatures, at ambient temperature, for example, for certain processes that use light hydrocarbons.

The invention is applicable to any catalytic process that operates at least partly in the liquid phase with a feedstock that contains carbon-containing substances, especially hydrocarbons.

The invention thus pertains to a continuous catalytic process that uses a catalyst circulating in a moving bed in at least one reaction zone that operates in the liquid phase and in a regenerator, with a lift to transfer the deactivated catalyst emerging from the reaction zone to the regenerator, whereby said process is characterized by the fact that the transfer is accomplished by a gas that does not react with the catalyst and with the stripping off of at least a portion of the organic matter that is adsorbed on the deactivated catalyst.

More particularly, the invention pertains to a metathesis process and, preferably, to a process for metathesis of olefins having 2–40 carbon atoms, preferably 2–30 carbon atoms, or advantageously 2–10 carbon atoms, and more specifically the C4, C5, C6 olefins or heavier olefins (C18–C30), between them (the same or different olefins) or ethylene or propylene.

The catalyst circulates in a descending moving bed, continuously or in batch mode.

The deactivated (i.e., at least partly deactivated) catalyst that contains adsorbed organic matter (hydrocarbons, for example) is transferred to the regenerator by a stripper-lift.

The transfer is accomplished under the action of at least one gas that does not react with the catalyst under the conditions of the process; this may be nitrogen, methane, or ethane, for example. The gas that is used is also intended to strip off at least a portion of the adsorbed organic matter, such that a catalyst that contains no more than 10% by weight of total organic matter (gums+coke+adsorbed material) arrives at the regenerator. However, before the catalyst is subjected to the action of said gas, the catalyst contains at least 10% by weight of total organic matter. The organic matter is mainly adsorbed organic matter; there may or may not be coke, and in all cases less than 10% coke by weight, and more generally less than 8% coke by weight.

In metathesis, there are only adsorbed hydrocarbons; coke is not formed. The invention thus applies especially well to the catalytic processes that operate at temperatures below the point at which coke forms on the catalyst.

It has been found that in the process according to the invention the ratio of adsorbed organic matter to catalyst at the inlet to the stripper-lift is 0.50% (by weight) or else 1–50% or 2–50%, and more particularly 5–20% (by weight), and at the outlet it is 0–10% (by weight) and preferably 1–6% (by weight).

The speed of the solid in the stripper-lift is generally 1–10 m/sec, and preferably 2–5 m/sec. The ratio of catalyst to gas (in $kg/cm^3$) is generally between 1 and 20, and advantageously between 5 and 12. The temperature of the gas is variable: 0–400° C., but more generally 10–150° C., for metathesis for example. The pressure of the gas can be up to 5.0 MPa, and more particularly 0.02–0.7 MPa for metathesis.

BRIEF DESCRIPTION OF THE DRAWING

The attached is a schematic flowsheet of an embodiment of the invention wherein metathesis is conducted.

DETAILED DESCRIPTION OF THE DRAWING

An advantageous metathesis process is shown in FIG. 1. In this process the catalyst circulates in a moving bed in at least one reaction zone where metathesis is carried out, and then the catalyst is separated from the residual liquid and depressurized before being lifted with stripping by a gas, whereby the gas is separated from the catalyst. The catalyst is regenerated (in the gas phase) and transferred by a lift to at least one zone where separation of the gas from the lift, repressurization, and wetting of the catalyst take place, and then the catalyst is reintroduced under a liquid into the reaction zone.

The invention also pertains to an installation for implementing a metathesis process, whereby said installation includes:

- at least one reaction zone 1 that operates in the liquid phase and that is equipped with at least one pipe 3 for introducing the feedstock to be treated, at least one pipe 4 for the discharge of the products, at least one pipe 31 to let in the catalyst, and at least one pipe 5 for the removal of the catalyst, whereby the catalyst circulates in a moving bed;
- at least one depressurization hopper 6 that is equipped with at least one pipe 7 for removal of the residual liquid;
- at least one stripper-lift 11, which receives the catalyst via a pipe 9 and is equipped with a drive-gas inlet pipe 10;
- at least one hopper 12 for separation of the drive gas that is evacuated via pipe 13, at least one regenerator 16 with a catalyst feed tube 32, at least one tube 17 to let in at least one oxygen-containing gas, at least one pipe 18 for the discharge of the gaseous effluent, and at least one tube 25 for the discharge of the catalyst, whereby the catalyst flows into the moving-bed regenerator;
- at least one lift 27, which is equipped with at least one tube 26 to let in the drive gas;
- at least one hopper 28 for the separation of the drive gas that is evacuated via pipe 29, whereby the repressurization by a pressurized gas comes from tube 35 and the wetting of the catalyst is accomplished by a liquid that arrives via at least one tube 34, whereby the catalyst is evacuated via a pipe 31 to the reaction zone.

Generally, stripper-lift 11 and lift 27 have at their bases lift pots (8 and 24, respectively), into which flow the catalyst to be lifted and the drive gas.

In an advantageous embodiment, the installation also includes:

- at least one buffer tank 14, which is located between hopper 12 and regenerator 16;
- at least one inerting hopper 21, which is located between regenerator 16 and pot 24 and is equipped with at least one pipe 23 for introducing the inert gas and in which a hopper 28, which receives the catalyst from lift 27, is equipped with at least one pipe 29 for the discharge of the separated drive gas and at least one tube 33 to let in an elutriation gas, and in another hopper 2 which is located between hopper 28 and reaction zone 1, which is equipped with at least one pipe 34 to let in a wetting liquid and in which repressurization can be carried out advantageously (if necessary) for the process being used.

Moreover, in cases where the drive gases of the lifts are the same, the gases that are separated in pipes 13 and 29 have their catalyst fines removed and are re-compressed and recycled via pipes 33, 10, 26 to, respectively, hopper 28, pot 8, and pot 24.

The invention is depicted in FIG. 1 for a metathesis process more specifically, but it is applicable to any catalytic process.

FIG. 1 shows the circulation of the catalyst in a moving-bed metathesis process.

The catalyst has been loaded into the reactor or reaction zone 1 (there could be multiple reaction zones). One or more tubes to supply new catalyst during the operation of the installation may be provided at, for example, a pressurization hopper (or tank) 2 that is located just upstream from reactor 1 (in the direction of flow of the catalyst).

In this hopper, repressurization and wetting of the catalyst particles are carried out.

The catalyst circulates in reaction zone 1 where it is brought into contact with the feedstock that is to be treated and is introduced via pipe 3. The products that are obtained as a result of the reaction exit via a pipe 4. The feedstock has been depicted here flowing upward, but a downward flow can also be envisioned in the process according to the invention.

The catalyst that emerges from reactor 1 via pipe 5 moves into a hopper (or tank) 6 in which depressurization takes place, whereby the residual liquid is separated from the solid particles of the catalyst and is evacuated via a pipe 7.

The catalyst that is drained in this way enters into lift pot 8 via a pipe 9. The gas that serves to lift and strip the catalyst is introduced into pot 8 via a tube 10, optionally after being reheated in a device 37.

Stripper-lift 11, which is formed by a tube, makes it possible to transfer the catalyst into a hopper (or tank) 12 where the gas is separated from the catalyst and leaves the hopper via a tube 13. The gas is evacuated via line 13 either to flare 38 if it contains hydrocarbons, or it is recycled if it is inert.

The catalyst is then advantageously transferred into a buffer-hopper 14 via a tube 15 in order to be able to ensure a continuous flow of catalyst through regenerator 16 (which includes at least one regeneration zone in which the catalyst circulates in a moving bed) via a tube 32.

The regenerator also includes at least one tube 17 to let in at least one oxygen-containing gas and at least one tube 18 for the discharge of the gaseous effluent arising from regeneration.

Preferably, the regenerator for metathesis includes at least one (and preferably one) combustion zone at the top of the regenerator that is supplied with an oxygen-containing gas via at least one tube 17, whereby the effluent originating from the combustion is discharged partly via at least one tube 19. Preferably, combustion takes place with a radial flow of the oxygen-containing gas.

The catalyst that emerges from the combustion zone then passes through at least one zone that provides for the calcination of the catalyst. An oxygen-containing gas enters via at least one pipe 20, and the resulting gaseous effluent leaves in turn via at least one pipe 18. Preferably, calcination is done with a radial flow of the oxygen-containing gas and, very advantageously, in a single zone.

To avoid cluttering up the figure, these zones were not depicted in greater detail.

The regenerated catalyst is then inert, i.e., it has undergone treatment by an inert gas (preferably nitrogen), so as to remove from the catalytic bed the traces of oxidizing gas or, more generally, the mixture of gas that is present in the regenerator. Preferably, inerting is carried out in a hopper 21 (tank) that is supplied with catalyst via a pipe 22 and with an inert gas via a pipe (pipes) 23. A large portion of the gas rises back up to the regenerator via tube 22 and is discharged with the gaseous effluent via tube 18. Inerting in a specific hopper is not absolutely necessary if the drive gas of the lift is nitrogen, but it is very preferable to implement it in this way.

The catalyst is then transferred to lift pot 24 via pipe 25 and, under the action of the gas that supplies the pot via tube 26, the catalyst is raised in lift 27 to a hopper 28 (or tank). Elutriation by gas arriving via a pipe 33 takes place in this hopper so as to separate the excessively fine catalyst particles and to remove them via a pipe 29 with the separated gas coming from the lift.

This gas is treated in order to separate the fines and is advantageously recycled after compression (compressor 36) for elutriation (hopper 28), stripper-lift 11, and lift 27. It is possible to include in this treatment the gas that exits via pipe 13 and has been used by the stripper-lift (as indicated in the figure).

The catalyst then descends via a pipe 30 to hopper 2. In addition to pressurizing the bed, it is also advantageous to wet the catalyst particles with a liquid that is brought in via at least one pipe 34. This is done, for example, in FIG. 1 with at least a portion of the residual liquid that is separated from the catalytic bed in hopper 6 and that circulates in pipe 7. Clearly, any arrangement is possible within the framework of this liquid loop (buffer tank, . . . ).

The catalyst, which is thus ready, is transferred to reactor 1 via pipe 31.

In the description given above, one pipe for transferring the catalyst between the hoppers, the reactor and the regenerator was considered, but multiple pipes are possible.

It is particularly advantageous for the drive gases of the lifts to be the same, but different drive gases can also be employed.

The preceding specific embodiments are to be construed as merely illustrative, and not limitative of the remainder of the disclosure in any way whatsoever.

The entire disclosure of all applications, patents and publications, cited above and below, and of corresponding French application 98/09.823, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a catalytic olefin metathesis process comprising circulating a catalyst in a moving bed in at least one reaction zone operating in the liquid phase and in a regenerator, with a lift to transfer deactivated catalyst emerging from the reaction zone to the regenerator, the improvement comprising conducting the transfer with a gas that does not react with the catalyst and while stripping off of at least a portion of organic matter adsorbed on the deactivated catalyst, and wherein the speed of deactivated catalyst in the lift is 2–10 m/sec.

2. A process according to claim 1, in which the ratio by weight of adsorbed organic matter to catalyst at the inlet of the lift is 0.5–50% and at the outlet is 0–10%.

3. A process according to claim 2, in which the speed of the solid in the lift is 1–10 m/sec, the ratio of catalyst to gas is 1–20 (in kg/m$^3$), and the temperature of the gas is 0–400° C.

4. A process according to claim 3, for the metathesis of olefins that have 2–40 carbon atoms.

5. A process according to claim 2, for the metathesis of olefins that have 2–40 carbon atoms.

6. A process according to claim 1, in which the speed of the deactivated catalyst solid in the lift is 2–5 m/sec, the ratio of catalyst to gas is 1–20 kg/m$^3$, and the temperature of the gas is 0–400° C.

7. A process according to claim 6, for the metathesis of olefins that have 2–40 carbon atoms.

8. Process according to claim 1 for the metathesis of olefins that have 2–40 carbon atoms.

9. A process according to claim 8 for metathesis of olefins selected from the group consisting of $C_2$ to $C_6$, $C_{18}$ to $C_{30}$, and combination thereof.

10. A process according to claim 8 in which the catalyst circulates in a moving bed in at least one reaction zone where metathesis is carried out, the catalyst is then separated from the residual liquid and depressurized before being raised with stripping by a gas, whereby the gas is separated from the catalyst, and the catalyst is regenerated and transferred by a lift in at least one zone where the separation of the gas from the lift, the repressurization and wetting of the catalyst are accomplished, and then the catalyst is reintroduced into the reaction zone.

11. A process according to claim 10 for metathesis of C4 and/or C5 and/or C6 fractions or heavier fractions (C18–C30) between them or with ethylene or propylene.

12. A process according to claim 10, in which the ratio by weight of adsorbed organic matter to catalyst at the lift is 0.5–50% and at the outlet is 0–10%.

13. A process according to claim 12, in which the speed of the solid in the lift is 1–10 m/sec, the ratio of deactivated catalyst catalyst to gas is 1–20 in kg/m$^3$, and the temperature of the gas is 0–400° C.

14. A process according to claim 10, in which the speed of the solid in the lift is 1–10 m/sec, the ratio of deactivated catalyst catalyst to gas is 1–20 in kg/m$^3$, and the temperature of the gas is 0–400° C.

15. A process according to claim 1, wherein gas is nitrogen, methane or ethane.

16. A process according to claim 15, wherein the temperature of the gas is 10–150° C.

17. A process according to claim 15, wherein the temperature of the lift gas is ambient.

18. A process according to claim 1, wherein the temperature of the gas is 10–150° C.

19. A process according to claim 1, wherein the temperature of the lift gas is ambient.

20. In a catalytic process comprising circulating a catalyst in a moving bed in at least one reaction zone operating in the liquid phase and in a regenerator, with a lift to transfer deactivated catalyst emerging from the reaction zone to the regenerator, the improvement comprising conducting the transfer with a gas that does not react with the catalyst while stripping off of at least a portion of organic matter adsorbed on the deactivated catalyst and wherein the speed of deactivated catalyst in the lift is sufficient to entrain particles upwardly.

21. A process according to claim 20, wherein the speed of the deactivated catalyst in the lift is 1–10 m/sec.

22. A process according to claim 21, wherein the temperature of the gas is 10–150° C.

23. A process according to claim 20, wherein the temperature of the gas is 10–150° C.

24. In a catalytic process comprising circulating a catalyst in a moving bed in at least one reaction zone operating in the liquid phase and in a regenerator, with a lift to transfer deactivated catalyst emerging from the reaction zone to the regenerator, the improvement comprising conducting the transfer with a gas that does not react with the catalyst and while stripping off of at least a portion of organic matter adsorbed on the deactivated catalyst and wherein the temperature of the gas is 10–150° C.

25. In a catalytic process comprising circulating a catalyst in a moving bed in at least one reaction zone operating in the liquid phase and in a regenerator, with a lift to transfer deactivated catalyst emerging from the reaction zone to the regenerator, the improvement comprising conducting the transfer with a gas that does not react with the catalyst, while stripping off at least a portion of organic matter adsorbed on the deactivated catalyst.

* * * * *

UNITED STATES PATENT AND TRADEMARK OFFICE
CERTIFICATE OF CORRECTION

PATENT NO.    : 6,284,939 B1
DATED         : September 4, 2001
INVENTOR(S)   : Hoffmann et al.

It is certified that error appears in the above-identified patent and that said Letters Patent is hereby corrected as shown below:

Column 6,
Line 3, reads "(in $kg/m^3$)," should read -- $kg/m^3$ --
Line 13, reads "according to claim 6" should read -- according to claim 10 --
Line 34, reads "catalyst at the lift is" should read -- catalyst at the inlet of the lift is --
Line 38, reads "catalyst catalyst to gas is 1-20 in $kg/m^3$" should read -- catalyst to gas is 1-20 $kg/m^3$ --
Line 42, reads "catalyst catalyst to gas is 1-20 in $kg/m^3$" should read -- catalyst to gas is 1-20 $kg/m^3$ --

Signed and Sealed this

Twelfth Day of November, 2002

*Attest:*

JAMES E. ROGAN
*Attesting Officer*    Director of the United States Patent and Trademark Office